(12) United States Patent
Thuduppathy et al.

(10) Patent No.: US 10,059,770 B2
(45) Date of Patent: Aug. 28, 2018

(54) PROCESS OF MODULATING MAN5 AND/OR AFUCOSYLATION CONTENT OF A GLYCOPROTEIN COMPOSITION

(71) Applicant: DR. REDDY'S LABORATORIES LIMITED, Qutubullapur (IN)

(72) Inventors: Guruvasuthevan Ramasamy Thuduppathy, Coimbatore (IN); Paranandi Ananta Madhava Ram, Hyderabad (IN); Kaumil Bhavsar, Ahmedabad (IN); Neha Garg, Ambala (IN)

(73) Assignee: DR. REDDY'S LABORATORIES LIMITED, Qutubullapur (IN)

(*) Notice: Subject to any disclaimer, the term of this patent is extended or adjusted under 35 U.S.C. 154(b) by 276 days.

(21) Appl. No.: 14/374,163

(22) PCT Filed: Jan. 18, 2013

(86) PCT No.: PCT/IB2013/050485
§ 371 (c)(1),
(2) Date: Jul. 23, 2014

(87) PCT Pub. No.: WO2013/114245
PCT Pub. Date: Aug. 8, 2013

(65) Prior Publication Data
US 2015/0344579 A1  Dec. 3, 2015

(30) Foreign Application Priority Data
Jan. 30, 2012 (IN) .............. 334/CHE/2012

(51) Int. Cl.
| C07K 16/28 | (2006.01) |
| C12N 5/00 | (2006.01) |
| C12P 21/00 | (2006.01) |
| C12N 1/38 | (2006.01) |
| C07K 16/32 | (2006.01) |

(52) U.S. Cl.
CPC .......... C07K 16/2863 (2013.01); C07K 16/32 (2013.01); C12N 1/38 (2013.01); C12N 5/0018 (2013.01); C12P 21/005 (2013.01); C07K 2317/14 (2013.01); C07K 2317/41 (2013.01); C12N 2500/20 (2013.01); C12N 2500/34 (2013.01)

(58) Field of Classification Search
None
See application file for complete search history.

(56) References Cited
U.S. PATENT DOCUMENTS

| 6,528,286 | B1 | 3/2003 | Ryll |
| 7,972,810 | B2 | 7/2011 | Crowell et al. |
| 2005/0084933 | A1 | 4/2005 | Schilling et al. |
| 2008/0118501 | A1 | 5/2008 | Schindler et al. |
| 2011/0053223 | A1 | 3/2011 | Bayer et al. |
| 2011/0287483 | A1 | 11/2011 | Crowell et al. |
| 2013/0210075 | A1 | 8/2013 | Satakami et al. |

FOREIGN PATENT DOCUMENTS

| EP | 1092037 B1 | 12/2005 |
| EP | 1957630 B1 | 2/2016 |
| WO | 99/61650 A1 | 12/1999 |
| WO | 2007/070315 A2 | 6/2007 |
| WO | 2011/011674 A2 | 1/2011 |
| WO | 2011/019622 A1 | 2/2011 |
| WO | 2011/127322 A1 | 10/2011 |

OTHER PUBLICATIONS

International Search Report dated Jul. 4, 2013, for corresponding International Patent Application No. PCT/IB2013/050485.
Written Opinion dated Jul. 4, 2013, for corresponding International Patent Application No. PCT/IB2013/050485.
Schwarz and Aebi, "Mechanisms and principles of N-linked protein glycosylation", Current Opinion in Structural Biology, 2011, vol. 21, pp. 576 to 582.
Imai-Nishiya et al., "Double knockdown of α1,6-fucosyltransferase (FUT8) and GDP-mannose 4,6-dehydratase (GMD) in antibody-producing cells: a new strategy for generating fully non-fucosylated therapeutic antibodies with enhanced ADCC", BMC Biotechnology, BioMed Central, Nov. 30, 2007, vol. 7:84, pp. 1 to 13.
Wright and Morrison, "Effect of Altered CH2-associated Carbohydrate Structure on the Functional Properties and In Vivo Fate of Chimeric Mouse-Human Immunoglobulin G1", J. Exp. Med., Sep. 1994, vol. 180, pp. 1087 to 1096, The Rockefeller University Press.
Wright and Morrison, "Effect of C2-Associated Carbohydrate Structure on Ig Effector Function: Studies with Chimeric Mouse-Human IgG1 Antibodies in Glycosylation Mutants of Chinese Hamster Ovary Cells", The Journal of Immunology, 1998, vol. 160, pp. 3393 to 3402, The American Association of Immunologists.
Shields et al., "Lack of Fucose on Human IgG1 N-Linked Oligosaccharide Improves Binding to Human FcRIII and Antibody-dependent Cellular Toxicity", The Journal of Biological Chemistry, 2002, vol. 277—issue No. 30, pp. 26733 to 26740, The American Society for Biochemistry and Molecular Biology, Inc.
Mori et al., "Engineering Chinese Hamster Ovary Cells to Maximize Effector Function of Produced Antibodies Using FUT8 siRNA", Biotechnology and Bioengineering, Dec. 30, 2004, vol. 88—issue No. 7, pp. 901 to 908, Wiley Periodicals, Inc.

(Continued)

Primary Examiner — Suzanne M Noakes
Assistant Examiner — Jae W Lee
(74) Attorney, Agent, or Firm — Pergament & Cepeda LLP; Milagros A. Cepeda; Edward D. Pergament (57) ABSTRACT

Provided is a method for producing glycoprotein composition with an increased percentage of Man5 and/or afucosylated glycans. Use of manganese for increasing the percentage of Man5 and afucosylated glycans in glycoprotein composition is further provided.

13 Claims, 4 Drawing Sheets

(56) References Cited

OTHER PUBLICATIONS

Mori et al., "Non-fucosylated therapeutic antibodies: the next generation of therapeutic antibodies", Review, Cytotechnology, 2007, pp. 109 to 114, vol. 55, Springer.
Pacis et al., "Effects of Cell Culture Conditions on Antibody N-linked Glycosylation—What Affects High Mannose 5 Glycoform", Article, Biotechnology and Bioengineering, Oct. 10, 2011, pp. 2348 to 2358, vol. 108—issue No. 10, Wiley Periodicals, Inc.
Yamane-Ohnuki et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity", Biotechnology and Bioengineering, Sep. 5, 2004, pp. 614 to 622, vol. 87—issue No. 5, Wiley Periodicals, Inc.
Zhou et al., "Development of a Simple and Rapid Method for Producing Non-Fucosylated Oligomannose Containing Antibodies With Increased Effector Function", Article, Biotechnology and Bioengineering, Feb. 15, 2008, pp. 652 to 665, vol. 99—issue No. 3, Wiley Periodicals, Inc.
Marino et al., "A systematic approach to protein glycosylation analysis: a path through the maze", Nature Chemical Biology, Oct. 2010, pp. 713 to 723, vol. 6.
Burda and Aebi, "The dolichol pathway of N-linked glycosylation", Biochimica et Biophysica Acta, 1999, pp. 239 to 257, vol. 1426, Elsevier Science B.V.
Kaufmann et al., "Influence of Low Temperature on Productivity, Proteome, Protein and Phophorylation of CHO Cells", Biotechnology and Bioengineering, Jun. 5, 1999, pp. 573 to 582, vol. 63—issue No. 5.
Trummer et al., "Process Parameter Shifting: Part II. Biphasic Cultivation—A Tool for Enhancing the Volumetric Productivity of Batch Processes Using Epo-Fc Expressing CHO Cells", Biotechnology and Bioengineering, Aug. 20, 2006, pp. 1045 to 1052, vol. 94—issue No. 6, Wiley Periodicals, Inc.
Yoon et al., "Effect of Low Culture Temperature on Specific Productivity, Transcription Level, and Heterogeneity of Erythyropoietin in Chinese Hamster Ovary Cells", Biotechnology and Bioengineering, May 5, 2003, pp. 289 to 298, vol. 82—issue No. 3, Wiley Periodicals, Inc.
Moore et al., "Effects of temperature shift on cell cycle, apoptosis and nucleotide pools in CHO cell batch cultures", Cytotechnology,1997, pp. 47 to 54, vol. 23, Kluwer Academic Publishers, Netherlands.
Borys et al., "Culture pH Affects Expression Rates and Glycosylation of Recombinant Mouse Placental Lactogen Proteins by Chinese Hamster Ovary (CHO) Cells", Bio/Technology, Jun. 1993, pp. 720 to 724, vol. 11.
Muthing et al., "Effects of Buffering Conditions and Culture pH on Production Rates and Glycosylation of Clinical Phase I Antimelanoma Mouse IgG3 Monoclonal Antibody R24", Biotechnology and Bioengineering, Aug. 5, 2003, pp. 321 to 334, vol. 83—issue No. 3, Wiley Periodicals, Inc.
Communication pursuant to Art. 94(3) EPC dated Oct. 17, 2017, for corresponding European Patent Application No. EP 13 74 3691.
Extended European Search Report dated Jun. 23, 2015, for corresponding European Patent Application No. EP 13 74 3691.
Extended European Search Report dated May 8, 2015, for corresponding European Patent Application No. 13743456.
International Search Report dated Jul. 25, 2013, for corresponding International Patent Application No. PCT/IB2013/050444.
Written Opinion dated Jul. 25, 2013, for corresponding International Patent Application No. PCT/IB2013/050444.
Jure Strnad, "Optimization of Cultivation Conditions in Spin Tubes for Chinese Hamster Ovary Cells Producing Erythropoietin and the Comparison of Glycosylation Patterns in Different Cultivation Vessels", Biotechnol. Prog., 2010, pp. 653 to 663, vol. 26—issue No. 3, American Institute of Chemical Engineers.
Marchant et al., "Metabolic Rates, Growth Phase, and mRNA Levels Influence Cell-Specific Antibody Production Levels from In Vitro-Cultured Mammalian Cells at Sub-Physiological Temperatures", Mol Biotechnol, 2008, pp. 69 to 77, vol. 39, Humana Press Inc.
Patrick et al., "N-Linked Glycosylation is an Important Parameter for Optimal Selection of Cell Lines Producing Biopharmaceutical Human IgG", Biotechnol. Prog., 2009, pp. 244 to 251, vol. 25—issue No. 1, American Institute of Chemical Engineers.
Ruhaak et al., "Glycan labeling strategies and their use in identification and quantification", Anal Bioanal Chem, 2010, pp. 3457 to 3481, vol. 397.
Non-Final Office Action mailed by the USPTO dated Feb. 9, 2017, for corresponding U.S. Appl. No. 14/373,853.
Non-Final Office Action mailed by the USPTO dated Nov. 30, 2017, for corresponding U.S. Appl. No. 14/373,853.
Hossler et al., "Optimal and consistent protein glycosylation in mammalian cell culture", Glycobiology, 2009, pp. 936 to 949, vol. 19—issue No. 9, Oxford University Press.
Moore et al., "Apoptosis in CHO cell cultures: examination by flow cytometry", Cytotechnology, 1995, pp. 1 to 11, vol. 17, Kluwer Academic Publishers, Netherlands.

| Glycan Structure | Code | Glycan Structure | Code |
|---|---|---|---|
| | M3 | | M6 |
| | M3NAG | | G₂F |
| | M3NAGF | | M7 |
| | G₀ | | G₂SF |
| | G₀F | | M8 |
| | M5 | | G₂S₂F |
| | G₁A | | G₁AF |
| | G₁B | | G₁BF |

Mannose ◆
N-Acetyl Glucosamine ●
Galactose ■
2-AB Label ✦
Fucose ☐
Sialic acid ▷

Figure 4

PROCESS OF MODULATING MAN5 AND/OR AFUCOSYLATION CONTENT OF A GLYCOPROTEIN COMPOSITION

RELATED APPLICATION

This application is a National Stage Application under 35 U.S.C. § 371 of PCT International Application No. PCT/IB2013/050485 filed Jan. 18, 2013, which claims the benefit of Indian Provisional Application No. 334/CHE/2012, filed Jan. 30, 2012, all of which are hereby incorporated by reference in their entireties.

BACKGROUND

The invention describes a method for obtaining a glycoprotein composition with increased Man5 and/or afucosylated glycoforms.

Protein glycosylation is one of the most important post-translation modifications associated with eukaryotic proteins. The two major types of glycosylations in eukaryotic cells are N-linked glycosylation, in which glycans are attached to the asparagine of the recognition sequence Asn-X-Thr/Ser, where "X" is any amino acid except proline, and O-linked glycosylation in which glycans are attached to serine or threonine. N-linked glycans are of further two types—high mannose type consisting of two N-acetylglucosamines plus a large number of mannose residues (more than 4), and complex type that contain more than two N-acetylglucosamines plus any number of other types of sugars. In both N- and O-glycosylation, there is usually a range of glycan structures associated with each site (microheterogeneity). Macroheterogeneity results from the fact that not all N-glycan or O-glycan consensus sequences (Asn-X-Ser/Thr for N-glycan and serine or threonine for O-glycan present in the glycoproteins) may actually be glycosylated. This may be a consequence of the competitive action of diverse enzymes during biosynthesis and are key to understanding glycoprotein heterogeneity (Mariño, K., (2010) *Nature Chemical Biology* 6, 713-723).

The process of N-linked glycosylation begins co-translationally in the Endoplasmic Reticulum (ER) where a complex set of reactions result in the attachment of $Glc_3NAc_2Man_9$ (3 glucose, 2 N-acetylglucosamine and 9 mannose) to a carrier molecule called dolichol, that is then transferred to the appropriate point on the polypeptide chain (Schwarz, F. and Aebi M., (2011) *Current Opinion in Structural Biology,* 21:576-582 & Burda, P. & Aebi M., (1999) *Biochimica et Biophysica Acta (BBA)General Subjects Volume* 1426, Issue 2, Pages 239-257). The glycan complex so formed in the ER lumen is modified by action of enzymes in the Golgi apparatus. If the saccharide is relatively inaccessible, it is likely stay in the original high-mannose form. If it is accessible, then many of the mannose residues may be cleaved off and the saccharide further modified, resulting in the complex type N-glycans structure. In the cis-Golgi, mannosidase-1 may cleave/hydrolyze a high mannose glycan, while further on, fucosyltransferase FUT-8 fucosylates the glycan in the medial-Golgi (Hanrue Imai-Nishiya (2007), *BMC Biotechnology,* 7:84).

Thus the sugar composition as well as the structural configuration of a glycan structure depends on the protein being glycosylated, the cells/cell lines, the glycosylation machinery in the Endoplasmic Reticulum and the Golgi apparatus, the accessibility of the machinery enzymes to the glycan structure, the order of action of each enzyme and the stage at which the protein is released from the glycosylation machinery.

In addition to the "in vivo" factors listed above, "external factors" may also affect the glycan structure and composition of a protein. These include the conditions in which the cell line expressing the protein is cultured, such as the medium composition, the composition and timing of the feed, osmolality, pH, temperature etc.

Studies by Kaufman et al and Yoon et al show a reduction in protein sialylation upon decrease in temperature (Kaufman, H., Mazur X., Fussenegger, M., Bailey, J. E., (1999) *Biotechnol Bioeng.* 63, 573-578; Trummer, E., Fauland, K., et. al. (2006) *BiotechnolBioeng.* 94 1045-1052); Yoon S. K., Song, J. Y., Lee, G. M., (2003) *Biotechnol Bioeng.* 82: 289-298). Further, reducing temperature can increase overall protein production by prolonging cell viability, which should, in principle, improve glycosylation. (Moore A, Mercer J, Dutina G, Donahue C J, Bauer K D, Mather J P, Etcheverry T, Ryll T. (1997), *Cytotechnology.* 23:47-54).

Likewise, Borys et al has shown that a deviation from optimum pH results in decrease in the expression rate as well as the extent of glycosylation of proteins (Borys M. C., Linzer, D. I. H., Papoutsakis (1993), *BIO/technology* 11 720-724). The culture pH of a hybridoma cell line has been shown to affect the resulting galactosylation and sialylation of the monoclonal antibody (Muthing J, Kemminer S E, Conradt H S, Sagi D, Nimtz M, Karst U, Peter-Katalinic J. (2003) *Biotechnol Bioeng* 83:321-334).

Further, methods for altering glycosylation by culturing cells expressing glycoproteins in cell culture medium comprising metal ions, in particular manganese, have been described. Crowell et al. has shown that the addition of manganese to the cell cultures increased galactosylation which in turn facilitated an increase in O- and N-linked glycosylation (Crowell C K, Grampp G E, Rogers G N, Miller J, Scheinman R I., (2007), *Biotechnol Bioeng.* 96:538-549).

U.S. Pat. No. 7,972,810 describes a process for increasing the sialylation in hyperglycosylated erythropoietin by addition of manganese in the concentration range of 0.04-40 µM.

Studies by Pacis et al. show a decrease in mannose glycoforms upon supplementing cell culture medium with manganese. In particular glycoforms bearing mannose5 (Man5) glycans decreased from ~25% to ~14% in a medium of ~400 mOsm/Kg and from ~13% to ~5% in a medium of ~300 mOsm/Kg upon supplementation with 1 µM Manganese (Pacis, E., Yu, M., Autsen, J., Bayer, R. and Li, F. (2011), *Biotechnology and Bioengineering,* 108: 2348-2358. doi: 10.1002/bit.23200). Likewise, US2011/0053223 discloses a cell culture process for accumulation of mannose5 bearing glycoforms by culturing cells in medium comprising manganese at a concentration of 0.25 µM or less.

The structure and composition of the glycan moieties of a glycoprotein can have a profound effect on the safety and efficacy of therapeutic proteins, including its immunogenicity, solubility and half life. Antibodies with high mannose content have become of interest because of the differential clearances of the antibodies bearing Man5 glycans and Man7, 8 or 9 glycans. Studies by Wright and Morrison show faster clearances for antibodies bearing Man7, 8, 9 glycans when compared to Man5 glycans (Wright and Morrison, (1994), *J. Exp. Med.* 180:1087-1096, 1998, *J. Imnnmology,* 160:3393-3402). Further, high mannose antibodies that were generated with kifunensine treatment showed higher ADCC activity and greater affinity to FcγRIIIA (Zhou Q. et al., (2008), *Biotechnol Bioeng* 99(3):652-665). Binding to the FcγIII receptor is dependent on the fucose content of the Fc glycans where a reduction in fucose can increase effector function. Fucose-deficient IgG1 s have shown a significant enhancement of ADCC up to 100-fold (Mori K, (2007), *Cytotechnology* 55(2-3):109-114. and Shields R L. (2002), *J BiolChem* 277(30):26733-26740). As afucosyl antibodies have become recognized as having potentially higher therapeutic potency due to enhanced ADCC function, high mannose antibodies, in particular antibody composition with increase Man5 glycan which also lack fucose can be of immense therapeutic benefit.

The present invention describes a process of obtaining an antibody composition comprising an enhanced Man5 and/or afucosylated glycans. Further, the invention describes a method for enhancing Man5 glycans and afucosylated glycans in the antibody composition by culturing cells in a media supplemented with manganese.

SUMMARY

The invention describes a process wherein cells are cultured in presence of manganese to obtain a glycoprotein composition having increased Man5 and/or afucosylatedglycoforms. Further, the method describes culturing cells in the presence of manganese and maintained pH to obtain glycoproteins with increased Man5 and afucosylated glycoforms.

DETAILED DESCRIPTION OF THE INVENTION

Definitions

The "viable cell count" or "cell viability" is defined as number of live cells in the total cell population. For e.g. by 35-40% viability it is meant that 35-40 percent of the cells are viable in the culture conditions at that point of time.

The "seeding density" is defined as the number of cells that are placed into a bioreactor during cell passage or during production stage.

The term "osmolality" as used herein is defined as a measure of the osmoles of solute per kilogram of solvent (osmol/kg) and may include ionized or non-ionized molecules and may change during the cell culture process for e.g. by addition of feed, salts, additives or metabolites.

The term "temperature shift" as used herein refers to any change in temperature during the cell culture process. For the purpose of this invention, the initial temperature of the cell culture process is higher than the final temperature i.e. cells are subjected to a temperature downshift wherein cells are first cultured at a higher temperature for certain time period after which temperature is reduced, and cells are cultured at this lower temperature for a fixed period of time.

The term "glycan" refers to a monosaccharide or polysaccharide moiety.

The term "glycoprotein" refers to protein or polypeptide having at least one glycan moiety. Thus, any polypeptide attached to a saccharide moiety is termed as glycoprotein.

Figure 4:
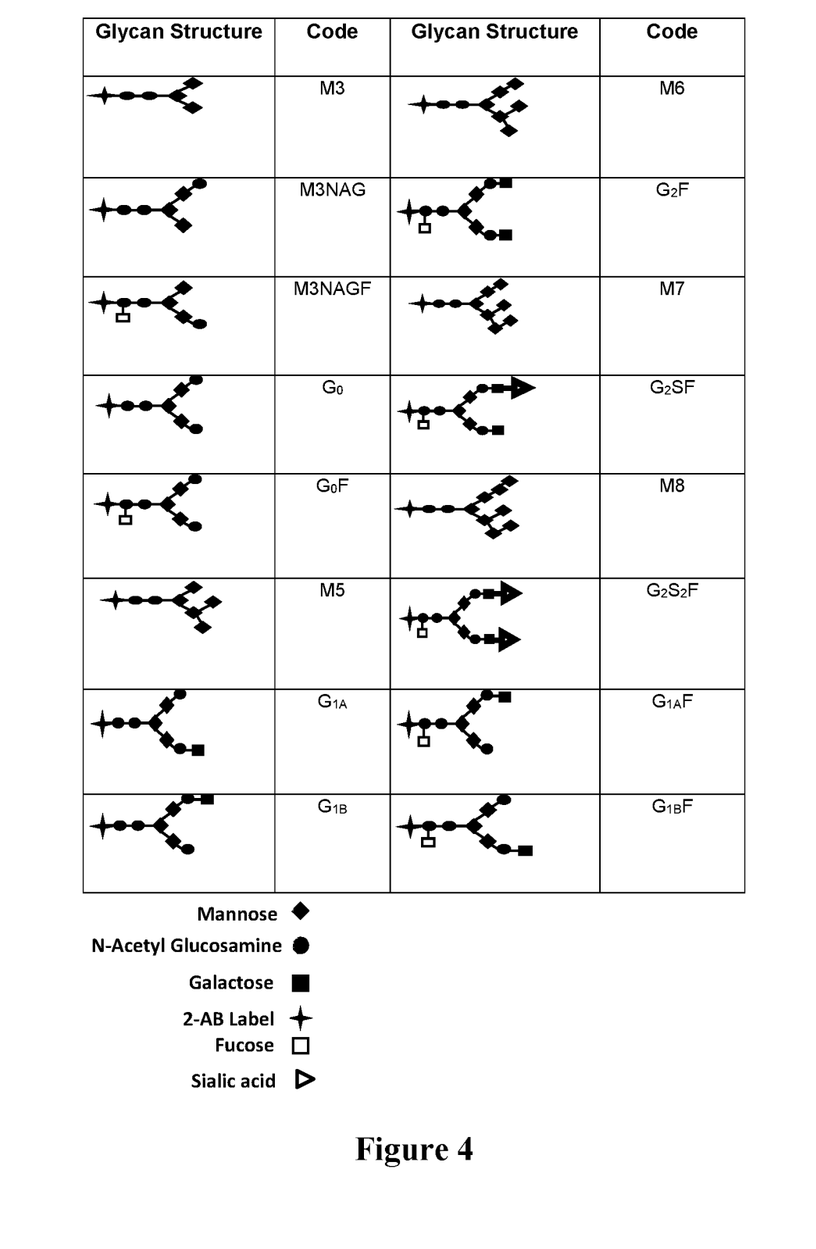
FIG. 4 is an illustration of the glycan moieties that may be added during protein glycosylation include M3, M4, M5-M8, M2NAG etc.

The term "glycoform" or "glycovariant" have been used interchangeably herein, and refers to various oligosaccharide entities or moieties linked in their entirety to the Asparagine 297 (as per Kabat numbering) of the human Fc region of the glycoprotein in question, co translationally or post translationally within a host cell. The glycan moieties that may be added during protein glycosylation include M3, M4, M5-8, M3NAG etc. Examples of such glycans and their structures are listed in FIG. 4. However, FIG. 4 may not be considered as limitation of this invention to these glycans.

The "glycoform composition" or distribution as used herein pertains to the quantity or percentage of different glycoforms present in a glycoprotein.

As used herein, "high mannose glycovariant" consists of glycan moieties comprising two N-acetylglucosamines and more than 4 mannose residues i.e. M5, M6, M7, and M8.

The "complex glycovariant" as used herein consists of glycan moieties comprising any number of sugars.

"Afucosylatedgly covariants or glycoforms" described here, consists of glycan moieties wherein fucose is not linked to the non reducing end of N-acetyglucosamine except the high mannose forms (for e.g. M3NAG, $G_0$, $G_{1A}$, $G_{1B}$, $G_2$).

$G_0$ as used herein refers to protein glycan not containing galactose at the terminal end of the glycan chain.

The present invention provides a cell culture method for obtaining a glycoprotein with increased percentage of Man5 and/or afucosylated glycoforms. In particular, the invention provides a cell culture process comprising culturing cells in the presence of manganese and maintained pH to obtain a glycoprotein composition with increased Man5 and afucosylated glycoforms.

Various methods described in the art such as Wuhreret. al., Ruhaak L. R., and Geoffrey et. al. can be used for assessing glycovariants present in a glycoprotein composition (Wuhrer M. et al., Journal of Chromatography B, 2005, Vol. 825, Issue 2, pages 124-133; Ruhaak L. R., Anal Bioanal Chem, 2010, Vol. 397:3457-3481 and Geoffrey, R. G. et. al. Analytical Biochemistry 1996, Vol. 240, pages 210-226).

In a first embodiment, the present invention provides a cell culture process for obtaining a glycoprotein composition with increased percentage of Man5 glycans comprising, culturing cells expressing said glycoprotein,
   a) in a medium comprising manganese
   b) at a pH about 6.8 to about 7.2
   c) recovering the protein from the cell culture.

In a further embodiment, the osmolality of the medium is in the range of about 350 mOsm/kg to about 600 mOsm/Kg.

In an embodiment the glycoprotein composition comprises about 8% to about 22% Man5 glycans.

In another embodiment the glycoprotein composition comprises about 8% Man5 glycans.

In yet another embodiment of the invention the glycoprotein composition comprises about 11% Man5 glycans.

In further embodiment the glycoprotein composition comprises about 13% Man5 glycans.

In yet another embodiment the glycoprotein composition comprises about 14% Man5 glycans.

In yet another embodiment the glycoprotein composition comprises about 22% Man5 glycans.

In a second embodiment, the present invention provides a cell culture process for obtaining a glycoprotein composition with increased percentage of afucosylated glycans comprising, culturing cells expressing said glycoprotein, a) in a medium comprising manganese
b) at pH of about 6.8 to about 7.2
c) recovering the protein from the cell culture In an embodiment the glycoprotein composition comprises about 4.5% to about 11% afucosylated glycans.

In another embodiment the glycoprotein composition comprises about 4.5% glycans.

In yet another embodiment the glycoprotein composition comprises about 5.5% afucosylated glycans.

In a further embodiment the glycoprotein composition comprises about 6.5% afucosylated glycans.

In yet another embodiment the glycoprotein composition comprises about 9% afucosylated glycans.

In yet another embodiment the glycoprotein composition comprises about 11% afucosylated glycans.

In a third embodiment, the present invention provides a cell culture process for obtaining a glycoprotein composition with increased percentage of Man5 glycans and afucosylated glycans comprising, culturing cells expressing said glycoprotein, a) in a medium comprising manganese
b) at pH of about 6.8 to about 7.2
c) recovering the protein from the cell culture In an embodiment the glycoprotein composition comprises about 4.5% to about 11% afucosylated glycans and about 8% to about 22% Man5 glycans.

In another embodiment the glycoprotein composition comprises about 4.5% afucosylated glycans and about 13% Man5 glycans.

In yet another embodiment the glycoprotein composition comprises about 5.5% afucosylated glycans and about 8% Man5 glycans.

In a further embodiment the glycoprotein composition comprises about 6.5% afucosylated glycans and about 14% Man5 glycans.

In yet another embodiment the glycoprotein comprises about 9% afucosylated glycans and about 11% Man5 glycans.

In yet another embodiment the glycoprotein composition comprises about 11% afucosylated glycans and about 22% Man5 glycans.

In another embodiment the cell culture process comprises culturing cells at a pH of about 6.8 to about 7.2 wherein the preferable pH is about 7.2.

In another embodiment the cell culture medium comprises about 0.35 µM to about 20 µM Manganese.

In yet another embodiment, the cell culture medium comprises about 1 µM Manganese.

In yet another embodiment, cell culture medium comprises about 2 µM Manganese.

In yet another embodiment, cell culture medium comprises about 20 µM Manganese.

Examples of useful salts of divalent manganese ions include, but are not limited to, manganese sulphate and manganese chloride.

In embodiments the cell culture process may be additionally accompanied by shift in temperature and addition of nutrient feed wherein the shift in temperature is towards lower values.

The cells may first be cultured at a temperature of about 35° C.-37° C. followed by lowering of temperatures by about 2-7° C.

In particular the cells may be cultured at about 37° C. followed by shifting the temperature to 35° C. In an alternate, cells may be cultured at about 37° C. followed by shifting the temperature to 33° C.

The pH in the cell culture media may be maintained by adding base to the cell culture medium for e.g. sodium carbonate.

The cell culture media that are useful in the application include but are not limited to, the commercially available products PF CHO (HyClone®), PowerCHO® 2 (Lonza), Zap-CHO (Invitria), CD CHO, CDOptiCHO™ and CHO-S-SFMII (Invitrogen), ProCHO™ (Lonza), CDM4CHO™ (Hyclone), DMEM (Invitrogen), DMEM/F12 (Invitrogen), Ham's F10 (Sigma), Minimal Essential Media (Sigma), and RPMI-1640 (Sigma).

The feeds in the present invention may be added in a continuous, profile or a bolus manner. Also it may be that one or more feeds are in one manner (e.g. profile mode) and others are in second mode (e.g. bolus or continuous mode). Further, the feed may be composed of nutrients or other medium components that have been depleted of metabolized by the cells. It may include hormones, growth factors, ions, vitamins, nucleoside, nucleotides, trace elements, amino acids, lipids or glucose. These supplementary components may be added at one time or in series of additions to replenish. Thus feed can be a solution of depleted nutrient(s), mixture of nutrient(s) or a mixture of cell culture medium/feed providing such nutrient(s). In one aspect of the invention, concentrated basal media may be used as a feed while in the other specific commercial feeds may be added to the cell culture medium.

Certain aspects and embodiments of the invention are more fully defined by reference to the following examples. These examples should not, however, be construed as limiting the scope of the invention.

EXAMPLE I

Figure 1:
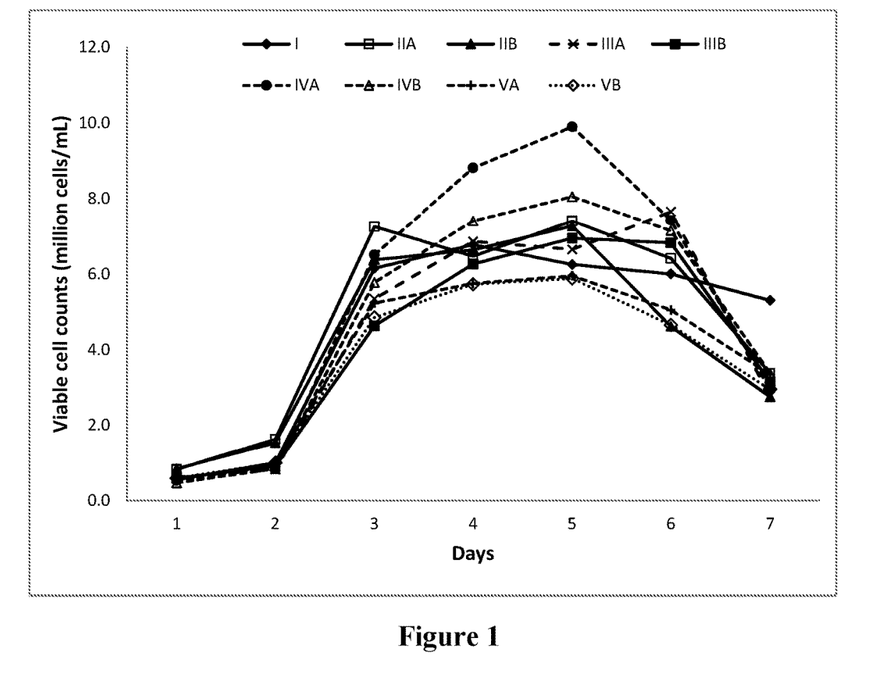
FIG. 1 is an illustration of effects of Manganese on the viable cell count during culture processes, as described in examples 1 to 5.
Figure 2:
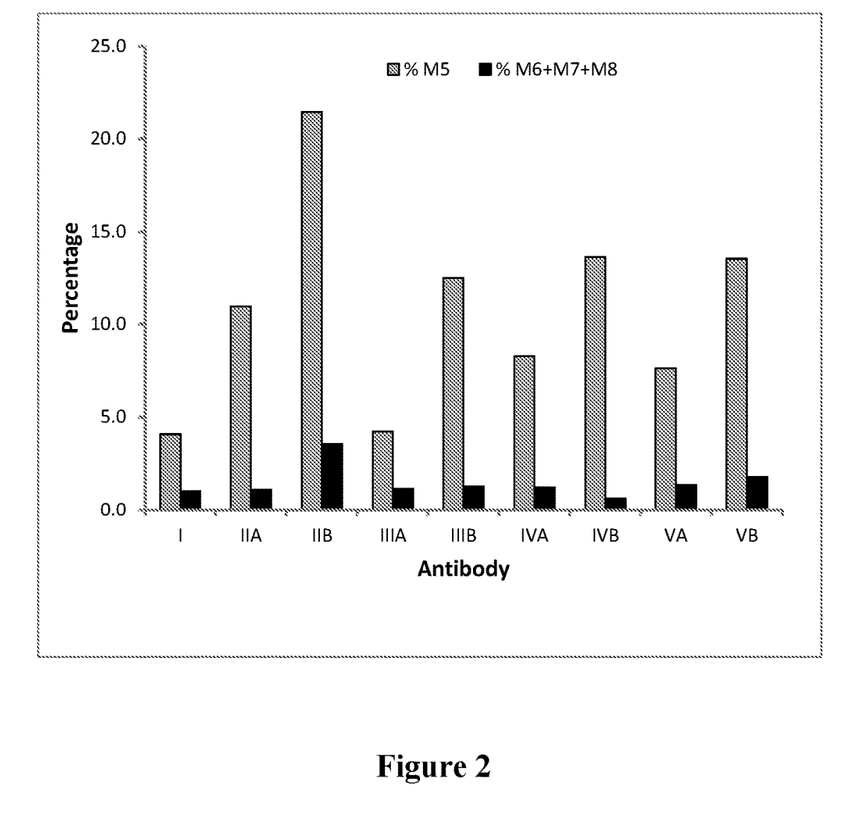
FIG. 2 is an illustration of effects of Manganese on Man5 and cumulative M6, M7 and M8 glycan content of the antibody composition obtained by processes described in examples 1 to 5.
Figure 3:
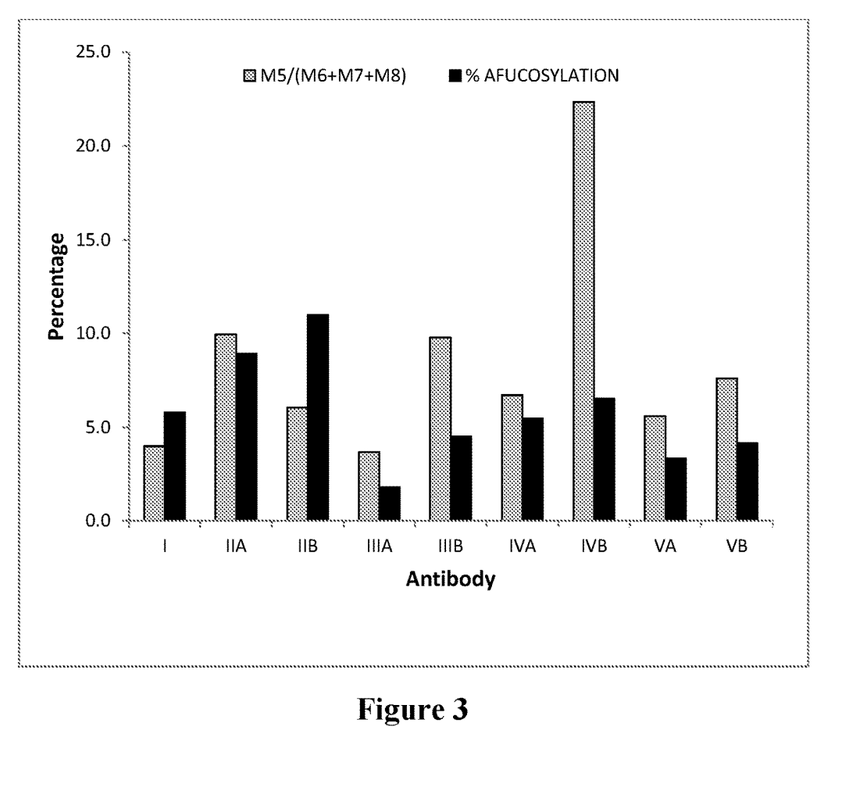
FIG. 3 is an illustration of effects of Manganese on Man5 and cumulative Man6, Man7, Man8 glycan ratio and afucosylation content of the antibody composition obtained by processes described in examples 1 to 5.

An anti-HER2 antibody was cloned and expressed in a CHO cell line as described in U.S. Pat. No. 5,821,337 which is incorporated herein by reference. The production bioreactor is initiated with the rCHO cells at seeding density of 0.4-0.6 million cells/ml in POWER CHO2 (Lonza, Catalog no: 12-771Q) media containing 6 g/L galactose at 37° C. and pH 7.2 at an osmolality of 290-370 mOsm/Kg. The feed (4% v/v 4× POWER CHO) is added at 48 and 72 hrs. At 96 hrs feed (4% v/v 4× POWER CHO) is added with a simultaneous shifting of temperature to 33° C. The cells are further cultured and harvested at 50% viability. The antibody (I) yield at harvest has been disclosed in Table I. The viable cell count, Man5 and afucosylation content are disclosed in FIGS. 1, 2 and 3.

EXAMPLE II

An anti-HER2 antibody was cloned and expressed in a CHO cell line as described in U.S. Pat. No. 5,821,337 which is incorporated herein by reference. The production bioreactor is initiated with the rCHO cells at seeding density of 0.4-0.6 million cells/ml in POWER CHO2 (Lonza, Catalog no: 12-771Q) media containing 6 g/L galactose at 37° C. and pH 7.2 at an osmolality of 290-370 mOsm/Kg. The medium is supplemented with manganese at concentration of 2 µM (IIA) or 20 µM (IIB). The feed (4% v/v of 4× POWER CHO) is added at 48 and 72 hrs. At 96 hrs feed (4% v/v of 4× POWER CHO) is added with a simultaneous shifting of temperature to 33° C. The cells are further cultured and harvested at 50% viability. The antibody yield at harvest has been disclosed in Table I. The viable cell count, Man5 and afucosylation content are disclosed in FIGS. 1, 2 and 3.

EXAMPLE III

An anti-HER2 antibody was cloned and expressed in a CHO cell line as described in U.S. Pat. No. 5,821,337 which is incorporated herein by reference. The production bioreactor is initiated with the rCHO cells at seeding density of 0.4-0.6 million cells/ml in POWER CHO2 (Lonza, Catalog no: 12-771Q) media containing 6 g/L galactose at 37° C. and pH 7.2 at an osmolality of 290-370 mOsm/Kg. The feed (8% v/v of IS F11.3, Irvine Scientific) is added at 48 and 72 hrs. At 96 hrs feed (8% v/v of IS F11.3) is added with simultaneous shifting of temperature to 35° C. More feeds (8% v/v each) are added at 120 hrs and 144 hrs. The cells are further cultured and harvested at 50% viability (IIIA).

In an alternate, the above process is performed as disclosed, except cell culture medium is supplemented with 2 µM Manganese and cells are harvested at 50% viability (IIIB). The antibody yield at harvest has been disclosed in Table I. The viable cell count, Man5 and afucosylation content are disclosed in FIGS. 1, 2 and 3.

EXAMPLE IV

An anti-HER2 antibody was cloned and expressed in a CHO cell line as described in U.S. Pat. No. 5,821,337 which is incorporated herein by reference. The production bioreactor is initiated with the rCHO cells at seeding density of 0.4-0.6 million cells/ml in POWER CHO2 (Lonza, Catalog no: 12-771Q) media containing 6 g/L galactose at 37° C. and pH 7.2 at an osmolality of 290-370 mOsm/Kg. The medium is supplemented with manganese at concentration of 1 µM (IVA) or 2 µM (IVB). The feed (4% of 4× POWER CHO) is added at 48 and 72 hrs. At 96 hrs feed (4% of 4× POWER CHO) is added with a simultaneous shifting of temperature to 35° C. The cells are further cultured and harvested at 50% viability.

The antibody yield at harvest has been disclosed in Table I. The viable cell count, Man5 and afucosylation content has been disclosed in FIGS. 1, 2 and 3.

EXAMPLE V

An anti-HER2 antibody was cloned and expressed in a CHO cell line as described in U.S. Pat. No. 5,821,337 which is incorporated herein by reference. The production bioreactor is initiated with the rCHO cells at seeding density of 0.4-0.6 million cells/ml in POWER CHO2 (Lonza, Catalog no: 12-771Q) media containing 3 g/L galactose at 37° C. and pH 7.2 at an osmolality of 290-370 mOsm/Kg. The feed (4% v/v of 4× POWER CHO and 3 g/L galactose) is added at 48 hrs. At 72 hrs temperature is shifted to 31° C. followed by addition of feed. More feeds are added at 96 hrs, 120 hrs and 144 hrs. The cells are further cultured and harvested at 50% viability (VA).

In an alternate, the above process is performed as disclosed, except cell culture medium is supplemented with 0.7 µM Manganese and cells are harvested at 50% viability (VB).

The antibody yield at harvest has been disclosed in Table I. The viable cell count, Man5 and afucosylation content has been disclosed in FIGS. 1, 2 and 3.

TABLE II

| Antibody titer at the time of harvest | |
|---|---|
| Examples | Final Titer(mg/l) |
| I | 722.0 |
| IIA | 720.0 |
| IIB | 550.0 |
| IIIA | 490.0 |
| IIIB | 500.0 |
| IVA | 440.0 |
| IVB | 430.0 |
| VA | 460.0 |
| VB | 416.0 |

We claim:

1. A cell culture process for obtaining an antibody composition comprising increased percentage of Man5 glycans and afucosylated glycans by culturing Chinese hamster ovary (CHO) cells expressing said antibody composition in culture medium comprising
   a) divalent manganese ion or its salts thereof at a concentration of 2 µM to 20 µM
   b) at a pH of about 6.8 to about 7.2
   c) recovering the antibody composition from the cell culture.

2. The process according to claim 1, wherein the antibody composition comprises about 4.5% to about 11% afucosylated glycans.

3. The process according to claim 1, wherein the antibody composition comprises about 8% to about 22% Man5 glycans.

4. The process according to claim 1, wherein the antibody composition comprises about 4.5% to about 11% afucosylated glycans and about 8% to about 22% Man5 glycans.

5. The process according to claim 1, wherein the said process further comprises addition of a feed.

6. The process according to claim 1, wherein the said process further comprises subjecting cells to a temperature shift wherein cells are cultured a) at first temperature for a first period of time and b) at second temperature for a second period of time.

7. A cell culture process for obtaining an antibody composition comprising increased percentage of Man5 glycans and afucosylated glycans by culturing CHO cells expressing said antibody composition in culture medium comprising the steps of:
   a) culturing the cells at a first temperature for a first period of time and a pH of about 6.8 to 7.2;
   b) supplementing the cells with divalent manganese ions or its salts thereof at a concentration of 2 µM to 20 µM;
   c) subjecting the cells to a temperature shift wherein the cells are cultured at a second temperature for a second period of time; and
   d) recovering the antibody composition from the cell culture.

8. The process according to claim 7, wherein the cells are first cultured at a first temperature of about 37° C.

9. The process according to claim 7, wherein the cells are shifted to a second temperature of about 31° C. to about 35° C.

10. The process according to claim 7, wherein the cells are shifted to a second temperature of about 35° C.

11. The process according to claim 7, wherein the cells are shifted to a second temperature of about 33° C.

12. The process according to claim 7, wherein the cells are shifted to a second temperature of about 31° C.

13. A cell culture process for obtaining an antibody composition comprising about 8% to about 22% of Man5 glycans and about 4.5% to about 11% of afucosylated glycans by culturing CHO cells expressing said antibody composition in culture medium comprising the steps of:
   a) culturing the cells at a first temperature of about 37° C. for a period of time and a pH of about 6.8 to 7.2:
   b) supplementing the cells with divalent manganese ions or its salts thereof at a concentration of 2 µM to 20 µM;
   c) subjecting the cells to a temperature shift and culturing the cells at a second temperature for a second period of time; and
   d) recovering the antibody composition from the cell culture.

* * * * *